United States Patent [19]
Norman et al.
[11] Patent Number: 4,845,254
[45] Date of Patent: Jul. 4, 1989

[54] NOVEL METAL-DIKETONE ABSORBENTS FOR CARBON MONOXIDE OR OLEFINS

[75] Inventors: John A. T. Norman, Whitehall; Robert E. Stevens, Emmaus, both of Pa.

[73] Assignee: Air Products and Chemicals, Inc., Allentown, Pa.

[21] Appl. No.: 167,605

[22] Filed: Mar. 14, 1988

Related U.S. Application Data

[62] Division of Ser. No. 83,742, Aug. 7, 1987, abandoned.

[51] Int. Cl.[4] .......... C07F 1/08; C07F 1/10
[52] U.S. Cl. .......... 556/41; 556/40
[58] Field of Search .......... 556/40, 41

[56] References Cited

U.S. PATENT DOCUMENTS

| | | | |
|---|---|---|---|
| 2,892,681 | 6/1959 | Crandall | 556/40 |
| 3,272,853 | 9/1966 | Brawn | 556/40 |
| 3,320,294 | 5/1967 | Larson | 556/40 |
| 3,401,112 | 9/1968 | Dunlop et al. | 208/308 |
| 3,424,772 | 1/1969 | Moshier | 556/40 |
| 3,578,619 | 5/1971 | Reeder | 556/40 |
| 3,592,865 | 7/1971 | Long et al. | 260/677 A |
| 3,764,274 | 10/1973 | Lucid | 568/412 |
| 3,794,433 | 2/1974 | Seeley | 568/412 |
| 3,864,407 | 2/1975 | Yates | 556/40 |
| 3,867,418 | 2/1975 | Burgett | 556/40 |
| 4,180,386 | 12/1979 | McCormack | 556/40 |
| 4,279,874 | 7/1981 | Doyle | 423/246 |
| 4,385,005 | 5/1983 | Doyle | 260/464 |
| 4,424,352 | 1/1984 | Siedle | 556/40 |
| 4,434,317 | 2/1984 | Doyle et al. | 585/845 |
| 4,471,152 | 9/1984 | Doyle et al. | 585/848 |
| 4,508,694 | 4/1985 | Doyle et al. | 423/246 |

FOREIGN PATENT DOCUMENTS

| | | |
|---|---|---|
| 3301225 | 7/1984 | Fed. Rep. of Germany . |
| 58-152836 | 9/1983 | Japan . |
| 1121905 | 8/1985 | United Kingdom . |

OTHER PUBLICATIONS

Doyle et al., *Organometallics*, vol. 4 (1985), pp. 830–835.
Walker, *Chemtech*, May 1975, pp. 308–311.
Bertholet, *Ann. de Chim. et de Phys.*, 7th series, vol. XXIII (May, 1901), pp. 32–39.
Bruce, *J. Organometal. Chem.*, vol. 44 (1972), pp. 209–226.
Gilland et al., *J. Am. Chem. Soc.* vol. 61 (1941), pp. 1960–1962; vol. 63 (1941), pp. 2088–2090.
Hurtado et al., *Transition Metal Chem.*, vol. 2 (1977), pp. 91–94.
Hartley et al., *J. Chem. Soc. Dalton* (1977), pp. 469–477.
Liebig, *Ann. der Pharmacie*, vol. IX (1834), pp. 1–39; vol. 23 (1837), pp. 12–42.
Lu're et al., *Sinet. Kauchuk*, vol. 3 (1934), pp. 19–29.
Winstein et al., *J. Am. Chem. Soc.*, vol. 60 (1938), pp. 836–847.
Kamitori et al., *Synthesis*, (Apr., 1986), pp. 340–342.
Vorob'eva et al., *Chem. Abs.*, 54:9987i.

*Primary Examiner*—Michael L. Shippen
*Attorney, Agent, or Firm*—Mark L. Rodgers; William F. Marsh; James C. Simmons

[57] ABSTRACT

Novel compounds for absorbing carbon monoxide and olefinically-unsaturated compounds from feedstreams are of the formula $$O{=}\underset{R_1}{\underset{|}{C}}{-}CR_2M^I{-}\underset{R_3}{\underset{|}{C}}{=}O$$

wherein $R_1$ is trichloromethyl or $R_F$; $R_F$ is $C_nF_{2n+1}$ and n is 1–8; $R_2$ is H or hydrocarbyl of 2–20 carbon atoms having at least one olefinic unsaturated bond; $M^I$ is $Cu^I$ or $Ag^I$ and $R_3$ is hydrocarbyl of 2–20 carbon atoms having at least one olefinic unsaturated bond.

9 Claims, 1 Drawing Sheet

NOVEL METAL-DIKETONE ABSORBENTS FOR CARBON MONOXIDE OR OLEFINS

This is a division of application Ser. No. 083,742, filed Aug. 7, 1987, now abandoned.

TECHNICAL FIELD

This invention relates to novel metal-containing complexes, which selectively absorb carbon monoxide or olefinically-unsaturated compounds from feedstreams.

BACKGROUND ART

Carbon monoxide is produced in a variety of incomplete oxidation processes. It appears in refinery off gas, methanol plant purge gas, blast furnace gas, water gas, coke oven gas and the gaseous effluent of steam reforming of methane. It would be highly desirable to isolate and use this carbon monoxide as a feedstock for other processes, for example, in making acetic acid. Methods for separating carbon monoxide from gas mixtures have been developed, including cryogenic distillation methods. These procedures are expensive. Therefore, there is a need for economical chemical processes for removing carbon monoxide from feed streams and recovering relatively pure carbon monoxide at the end of the separation process. Chemical separation processes are accordingly based on reversible binding of carbon monoxide with an absorbent, which will release carbon monoxide under appropriate conditions.

The separation of olefins from other hydrocarbons, including saturated hydrocarbons and aromatic hydrocarbons, is also of commercial interest. Although this can be accomplished by distillation, there is considerable interest in chemical processes, depending on selective complexation of one of a mixture of unsaturated hydrocarbons with an absorbent, which will release the hydrocarbon of interest under selected conditions.

The use of various metallic complexes has been investigated for the separation of both carbon monoxide and olefins from feed streams.

Doyle (U.S. Pat. No. 4,385,005) has proposed the use of a mixture of copper(I) or silver(I) oxide and a perfluorinated acetylacetonate to remove unsaturated hydrocarbons from feedstreams.

Carbon monoxide and alkene derivatives of copper(I) and silver(I) betadiketonates have been reported by Doyle et al., *Organometallics*, vol. 4 (1985), pages 830–835. These complexes are of varying stability with respect to air oxidation and disproportionation, but are insensitive to moisture.

Doyle has proposed in U.S. Pat. No. 4,279,874, using Cu(I) halogenated acetylacetonate complexes for the separation of carbon monoxide from a gas stream.

The use of Cu(I) complexes of fluorinated acetylacetone in an organic solvent for the removal of unaturated hydrocarbons from feedstreams has been proposed by Doyle et al. in U.S. Pat. Nos. 4,434,317 and 4,508,694. The use of a stabilized cuprous fluorinated acetonylacetonate is proposed by Doyle et al. in U.S. Pat. No. 4,471,152.

Long et al. (U.S. Pat. No. 3,592,865) have recited using cuprous aluminum halide complexes to remove complexible ligands from feedstreams.

Walker, "Making and using CO," *Chemtech* (May, 1975), pages 308–311, has described the Cosorb purification process for separating carbon monoxide from gaseous mixtures, including streams rich in nitrogen. The process relies on stabilization of the active component, cuprous tetrachloroaluminate, in an aromatic solvent.

Dunlop et al., in U.S. Pat. No. 3,401,112, have recited separating hydrocarbons of various kinds of unsaturation using cuprous salts of oxyacids.

References suggesting the state of the art of metal complexes, using organic or inorganic copper(I) or silver(I) compounds, include:

M. Bertholet, "Observations Relatives a L'action des Sels Cuivreux sur les Carbures D'hydrogene et sur L'oxyde de carbon," *Ann. de Chim. et de Phys.*, 7th series, vol. XXIII (May, 1901), pages 32–39

M. I. Bruce, "Carbonyl Chemistry of the Group IB Metals," *J. Organometal. Chem.*, vol. 44 (1972), pages 209–228

E. R. Gilliland et al., "Reactions of Olefins with Solid Cuprous Halides," *J. Am. Chem. Soc.*, vol. 61 (1939), pages 1960–1962; ibid., vol. 63 (1941), pages 2088–2090

R. J. Hurtado et al., "Copper(I) Nitrile Complexes, Part III. Reversible Olefin Complex Formation with Acetonitrilecopper(I) Trifluoromethanesulfonate," *Transition Met. Chem.*, vol. 2 (1977), pages 91–94

F. R. Hartley et al., "Influence of Solvent on the Stability of Silver(I)-Olefin Complexes," *J. Chem. Soc. Dalton* (1977), pages 469–477

J. Liebig, "Ueber die Constitution des Aethers und seiner Verbindungen," *Ann. der Pharmacie*, vol. IX (1834), pages 1–39; "Ueber die Aethertheorie, in besonderer Rücksicht auf die vorhergehende Abhandlung Zeise's", ibid., vol. 23 (1837), pages 12–42

M. A. Lur'e et al., "Separation of 1,3-Butadiene from a Mixture of Other Hydrocarbons Using Cuprous Chloride," *Sinet. Kauchuk*, vol. 3, no. 6 (1934), pages 19–29

S. Winstein et al., "The Coordination of Silver Ion with Unsaturated Compounds," *J. Am. Chem. Soc.*, vol. 60 (1938), pages 836–847.

Kamitori et al., *Synthesis*, April, 1986, pages 340–342, have recited the preparation of 3-allyl-1,1,1-trifluoroacetylacetone and related compounds, which are useful as chelating agents.

DISCLOSURE OF INVENTION

In one aspect, this invention relates to novel unsaturated trichloromethyl or perfluoroalkyl diketones of the formula

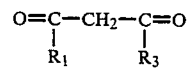

wherein $R_1$ is trichloromethyl or $R_F$; $R_F$ is $C_nF_{2n+1}$ and n is 1–8; and $R_3$ is hydrocarbyl of 2–20 carbon atoms having at least one olefinic unsaturated bond.

In another aspect, this invention relates to $Cu^I$ or $Ag^I$ complexes of perfluoroalkyl diketonate compounds, having the formula

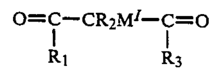

wherein $R_1$ and $R_3$ are as above, $M^I$ is $Cu^I$ or $Ag^I$ and $R_2$ is H or hydrocarbyl of 2–20 carbon atoms having at least one olefinic unsaturated bond.

This invention further relates to a process for removing carbon monoxide or an unsaturated hydrocarbon containing at least one olefinic unsaturated bond from a feedstream by contacting the feedstream with a metal-diketonate compound, as above, in an inert organic solvent or vehicle.

In yet another aspect, this invention relates to compounds of the formula

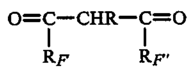

wherein $R_F$ and $R_{F'}$ are independently selected from perfluoroalkyl of 1–8-carbon atoms and R is hydrocarbyl of 2–20 carbon atoms having at least one olefinic unsaturated bond.

This invention further relates to novel metal-diketone compounds of the formula

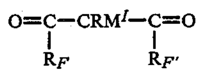

wherein $R_{F'}$, $R_{F''}$, and R and $M^I$ are as above, as well as to their use as absorbents for carbon monoxide and olefins in feed streams.

In a further aspect, this invention relates to a process for making compounds of the formula

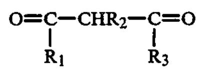

wherein $R_1$, $R_2$ and $R_3$ are as above, comprising the steps of:

(a) treating a ketone of the formula $R_2CH_2COR_3$ with lithium diisopropylamide to produce a compound of the formula $R_2CHCOR_3{}^-Li^+$; and (b) reacting thus-produced $R_2CHCOR_3{}^-Li^+$ with a compound of the formula $R_FCOOalk$ or $CCl_3COOalk$, wherein $R_F$ is as above and alk is alkyl of 1–6 carbon atoms, to produce the desired compound.

The trichloromethyl or perfluoroalkyl diketones of this invention can exist in two tautomeric forms, enol or ketone, corresponding to

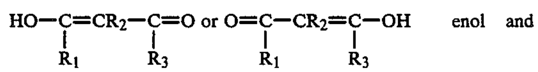

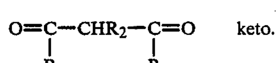

Alternatively, the tautomeric mixture can be represented by the formula

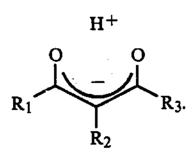

The perfluoroalkyl or trichloromethyl diketones are made from an unsaturated ketone of the formula $R_2CH_2COR_3$, wherein $R_2$ and $R_3$ are as above. This is converted to a lithio derivative, represented by the formula $R_2CHLiCOR_3$ by reaction with lithium diisopropylamide under anhydrous conditions. The resulting anion $^-R_2CHCOR_3$ adds to the carbonyl of $R_FCOOalk$ or $CCl_3$ COOalk to produce a beta-diketonate, which is protonated to the desired product, that is, to $R_1COCHR_2COR_3$.

Preferred diketone derivatives of this invention are those derived from trifluoroacetylacetone. It is therefore preferred to react a lithiated unsaturated ketone with a trifluoroacetate ester, most preferably with ethyl trifluoroacetate. It is preferred to carry out reactions in which $R_2CCH_2COR_3$ is 5-hexen-2-one, 6-methyl-5-hepten-2-one, geranyl acetone, neryl acetone, 3-prenyl-2-decanone or farnesyl acetone. In each of these cases, $R_2$ is H.

Preferred compounds of this invention include, but are not limited to:

1,1,1-trifluoro-7-octene-2,4-dione (ATFAC, allyltrifluoroacetoacetate), $R_1$ is $CF_3$, $R_2$ is H and $R_3$ is 1-butenyl, having the structure (enol form)

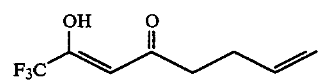

1,1,1-trifluoro-8-methyl-7-nonene-2,4-dione (OTFAC, olefin-trifluoroacetoacetate), $R_1$ is $CF_3$, $R_2$ is H and $R_3$ is 2-methyl-2-pentenyl, having the structure

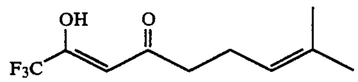

1,1,1-trifluoro-5-prenyl-dodecane-2,4-dione (HOTFAC, heptylated olefin-trifluoroacetoacetate), $R_1$ is $CF_3$, $R_2$ is H and $R_3$ is 5-(2-methyl-2-dodecenyl), having the structure

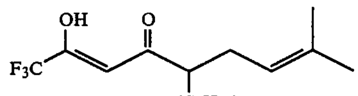

1,1,1-trifluoro-8,12-dimethyl-trans-7,11-tridecadiene-2,4-dione (GTFAC, geranyltrifluoroacetoacetate), $R_1$ is $CF_3$, $R_2$ is H and $R_3$ is (E)-2,6-dimethyl-2,6-nonadienyl, having the structure

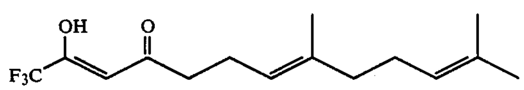

1,1,1-trifluoro-8,12-dimethyl-cis-7,11-tridecadiene-2,4-dione (NTFAC, neryltrifluoroactetoacetate), $R_1$ is $CF_3$, $R_2$ is H and $R_3$ is (Z)-2,6-dimethyl-2,6-nonadienyl, having the structure

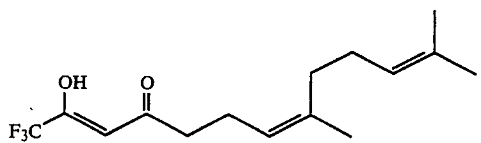

and 1,1,1-trifluoro-8,12,16-trimethyl-7,11,15-heptadecatriene-2,4-dione (FTFAC, farnesyltrifluoroacetoacetate), $R_1$ is $CF_3$, $R_2$ is H and $R_3$ is 2,6,10-trimethyl-2,6,10-tridecatrienyl (mixed EE, EZ, ZE and ZZ isomers), having the structure

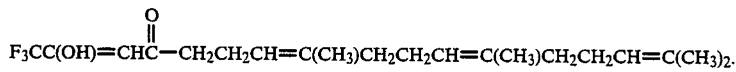

It will be understood that many of the compounds of this group contain a prenyl substituent and that compounds, containing a prenyl fragment, $-CH_2CH{=}C(CH_3)_2$, are among preferred TFAC-derived diketones.

The TFAC-derived diketones are converted to corresponding $M^I$ salts by reaction with a monovalent metal compound, preferably a compound of $Cu^I$ or $Ag^I$. It is preferred to use cuprous oxide, $Cu_2O$, of very high purity. It is most preferred to use $Cu_2O$ exceeding 99.9% purity. In order to obtain good yields of corresponding $Cu^I$-diketone compounds, it is preferred to use about half an equivalent of $Cu^I$ compound to TFAC-derived diketone. The structure of the monovalent metal salts can be represented by the formula:

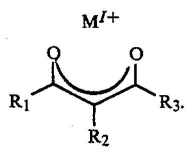

The $M^I$ complexes of $R_1COCHR_2COR_3$ are useful as absorbents for carbon monoxide and for hydrocarbons having at least one olefinically-unsaturated bond. The $Cu^I$ complexes are particularly preferred for the absorption of carbon monoxide, olefins or acetylenes from feedstreams.

Solutions or slurries of the absorbent complexes in an organic solvent are contacted with a stream containing carbon monoxide, an olefin or an acetylenic compound. The complexes bind carbon monoxide, the olefin or the acetylenic compound. The complexes, containing bound carbon monoxide, olefin or acetylenic compound, are isolated from the feed stream and further treated by heating or pressure reduction, or both, to liberate bound carbon monoxide, olefin or acetylenic compound. The complexes of this invention therefore provide an effective means for removal of carbon monoxide, olefins or acetylenic compounds from feed streams.

Most preferred absorbent compounds are $Cu^I$ complexes from 1,1,1-trifluoro-8,12-dimethyl-trans-7,11-tridecadiene-2,4-dione (GTFAC) and from 1,1,1-trifluoro-8-methyl-7-nonene-2,4-dione (OTFAC). The $M^I$ complexes are used for absorption of carbon monoxide or olefins in an inert organic solvent or diluent, particularly in ethylbenzene, toluene, cymene or the like.

An unexpected feature of the $Cu^{I+}{-}R_1COCR_2COR_3$ complexes is the low heat of absorption, about $-2$ to $-3$ keal/mol. The complexes are therefore very acceptable absorbents for carbon monoxide and olefins in feed streams.

Other compounds of this invention, useful as absorbents for carbon monoxide and olefins or other non-aromatic unsaturated hydrocarbons are those derived from diketones of the formula

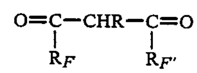

Compounds of this group can be made from a silver salt of a perfluorodiketone and an unsaturated halide, for example, allyl bromide. The following is typical of processes for making compounds of this type:

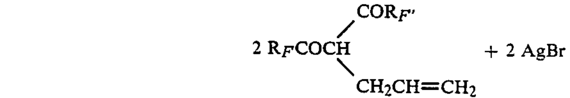

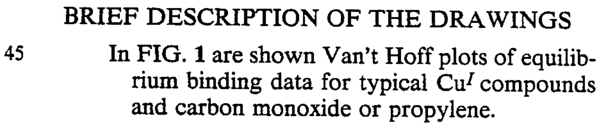

The diketones can be converted to $Cu^I$ or $Ag^I$ complexes by the same methods used for the TFAC-derived diketones. A most preferred compound of this series is a compound in which $R_F$ and $R_{F'}$ each are trifluoromethyl and R is allyl. A most preferred metal derivative is the $Cu^I$ derivative.

BEST MODE FOR CARRYING OUT THE INVENTION

Figure 1:
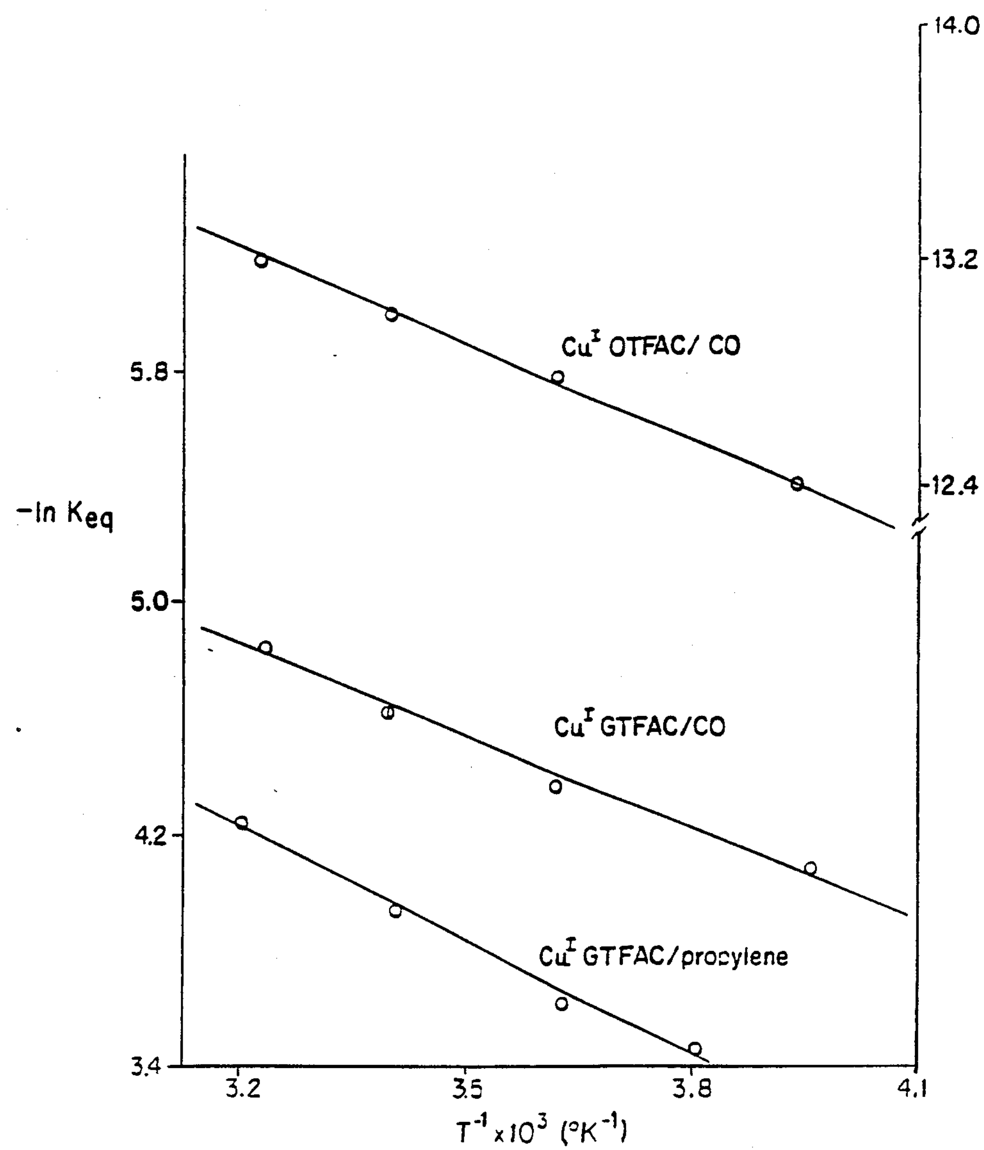
In FIG. 1 are shown Van't Hoff plots of equilibrium binding data for typical $Cu^I$ compounds and carbon monoxide or propylene.

Most preferred diketones of the invention are 1,1,1-trifluoro-7-octene-2,4-dione, 1,1,1-trifluoro-8-methyl-7-nonene-2,4-dione, 1,1,1-trifluoro-5-prenyl-do-decone-2,4-dione, 1,1,1-trifluoro-8,12-dimethyl-cis (or trans-)-7,11-tridecadiene-2,4-dione and 1,1,1-trifluoro-8,12,16-trimethyl-7,11,15-heptadecatriene-2,4-dione.

Most preferred are $Cu^I$ compounds derived from 1,1,1-trifluoro-8,12-dimethyltrans-7,11-tridecadiene-2,4-dione, 1,1,1-trifluoro-8-methyl-7-nonene-2,4-dione, 1,1,1-trifluoro-5-prenyl-dodecane-2,4-dione or 1,1,1-trifluoro-7-octene-2,4-dione.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following Examples, temperatures are set forth uncorrected in degrees Celsius or degrees Kelvin. Unless otherwise indicated, all parts and percentages are by weight.

5-Hexen-2-one, 6-methyl-5-hepten-2-one, ethyl trifluoroacetate, 1,1,1,5,5,5-hexafluoro-2,4-pentanedione, nerolidol, and lithium diisopropylamide (solid) were obtained from Aldrich Chemical Co. (940 West St. Paul Ave., Milwaukee, Wis. 53233). Geranyl acetone and neryl acetone were obtained from Fluka, Inc. (255 Oser Ave., Hauppauge, N. Y. 11788). 6,10-Dimethyl-5,9-undecen-2-one (E and Z mixture) was obtained from Wiley Co. (4654 Kenny Road, Columbus, Ohio 43220). Cuprous oxide (99.9%) was obtained from Cerac (407 North 13th St., Milwaukee, Wis. 53233).

Solvents used are HPLC grade. Hexane and tetrahydrofuran (THF) are distilled from calcium hydride under nitrogen. All operations in the preparation of the free ligands or corresponding complexes are carried out using standard Schlenk line techniques described by D. F. Shriver, "The Manipulation of Air-Sensitive Compounds," McGraw-Hill Publishing Co.

Farnesyl acetone is prepared from nerolidol by the method of Vorob'eva et al., *Zhur. Obshchei Khim.*, vol. 29 (1959), pages 2314–2318, abstracted in *Chem. Abs.*, vol. 54: 9987i.

Infrared spectra were obtained on a Perkin Elmer 684 spectrometer or a Nicolet 20 SXB spectrometer. $^1H$ NMR spectra were obtained using an IBM FY200 FT NRM spectrometer. Microananylses were performed by Research Services, Air Products & Chemicals, Inc. or Schwarzkopf Microanalytical Laboratory, Woodside, N. Y.

EXAMPLE 1

(a) Synthesis of Trifluoro-beta-diketone ligands of the TFAC (Trifluoroacetoacetate) Series Derivatives of TFAC are obtained by reaction between ethyl trifluoroacetate and a ketone. Lithium diisopropylamide (LDA, 11.8 g, 0.11 mol) is charged to a reaction flask, fitted with an addition funnel, inlet for nitrogen and magnetic stirring bar under an atmosphere of dry nitrogen. Rubber septa are fitted into the flask and funnel. THF (300 mL) is added to the contents of the flask and a further 20 mL is placed in the addition funnel. The ketone (0.1 mol) is charged to the addition funnel and the contents of the flask are cooled to −78° C. using an isopropanol/dry ice slush bath. The ketone is added dropwise to the stirred mixture over 20 min and stirring is continued at −78° C. for 10 min or more, after which the dry ice slush bath is removed and the resulting enolate solution is allowed to warm up to room temperature.

Ethyl trifluoroacetate (6.0 mL, 0.1 mol) is added by a syringe over 5 min, during which the reaction mixture darkens from a yellow color to a reddish color. The resulting mixture is stirred overnight, after which about 80% of the THF is removed using a rotating evaporator. The resulting concentrate is poured on to a 50/50 mixture of concentrated HCl/ice. The resulting mixture is extracted with three 100-mL portions of petroleum ether. The combined petroleum ether extracts are washed with three 100-mL portions of water, dried over anhydrous sodium sulfate, filtered and evaporated. The products are obtained in quantitative yield and are about 99% pure.

NMR spectra, IR spectra and elemental analyses for thus-prepared TFAC derivatives are given in Tables 1-3.

(b) Heptylation of OTFAC Ligand

6-Methyl-5-hepten-2-one (6.72 g, 0.052 mol) in 20 mL of THF is added over 20 min to a solution of LDA (0.53 g, 0.05 mol) in 200 mL of THF at −78° C. as above. The resulting mixture is stirred at −78° C. for 10 min and then allowed to warm to room temperature.

Heptyl iodide (11.3 g, 0.05 mol) is added to this mixture and stirring is continued overnight at room temperature. The intermediate is protonated by being poured over a 50/50 mixture of concentrated HCl/ice. The product is extracted into petroleum ether and isolated as above.

The crude reaction product is subjected to distillation under vacuum and the fractions screened by IR spectroscopy for ketone content by absorbance at about 1720 $cm^{-1}$. A fraction constituting 30% of the reaction product was found to be the desired ketone.

$^1H$ NMR, $CD_2Cl_2$: 0.83 ppm (t,3H); 1.25 ppm (bs,10H); 1.40 ppm (m, 2H); 1.58 ppm (3, 3H); 1.68 ppm (s, 3H); 2.05 ppm (s, 3H); 2.15 ppm (m, 2H); 2.4 ppm (m, 1H); 5.02 ppm (1H).

This ketone is subjected to reaction with ethyl trifluoroacetate as above to produce HOTFAC ligand. The ligand is isolated by chelation with $Cu^{II}$, using aqueous cupric acetate solution, and eluted through a column of Davisil silica gel MPLC column, using hexane initially to remove impurities and then 50/50 methylene chloride/hexane to give the $Cu^{II}$ complex (91% purity). The $Cu^{II}$ complex is treated with 200 mL of 6M HCl/methylene chloride (50:50 v/v) to liberate the free diketone. Characterization data for this compound are given in Tables 1-3.

TABLE 1

$^1H$ NMR in $CDCl_3$ for Trifluroacetoacetate (TFAC) Derivatives

| Ligand | $^1H$ NMR (δ) |
|---|---|
| ATFAC | 2.4 (t,2H); 2.55 (t,2H); 5.05(t,2H); 5.78(m,1H); 5.92(s,1H); 14.0(bs,1H) |
| OTFAC | 1.59(s,3H); 1.68(s,3H); 2.4(m,4H); 14.0(bs,1H) |
| HOTFAC | 0.9(t,3H); 1.25(s,10H); 1.6(s,5H); 1.66(s,3H); 2.25(m,3H); 5.0(m,1H); 5.85(s,1H); 14.3(bs,1H) |
| GTFAC | 1.57(s,3H); 1.59(s,3H); 1.66(s,3H); 2.0(m,4H); 2.4(m,4H); 5.06(m,2H); 5.89(s,1H); 14.2(bs,1H) |
| NTFAC | 1.58(s,3H); 1.66(s,6H); 2.02(d,4H); 2.39(m,4H); 5.06(t,2H); 5.88(s,1H); 14.5(bs,1H) |
| FTFAC* | 1.6(s, 6H); 1.7(s,6H); 2.0(d,8H); 2.4(m,4H); 5.1(t,3H); 5.9(s,1H); 12.5(bs,1H) |

*Mixture of regioisomers.

TABLE 2

| Ligand | IR Spectra for TFAC Derivatives (KBr plates, neat films) IR |
|---|---|
| ATFAC | 3086.0(m), 2984.8(m), 2926.9(m), 1643.8(s), 1601.2(s), 1448.9(m), 1419.7(m), 1366.7(m), 1282.8(s), 1203.3(s), 1156.1(s), 1110.1(s), 995.35(m), 920.03(m), 868.72(m), 882.17(m) $cm^{-1}$ |
| OTFAC | 2973.6(m), 2919.9(m), 2862.3(m), 1599.1(s), 1451.9(m), 1412.5(m), 1379.0(m), 1282.6(s), 1202.8(s), 1109.1(s), 875.28(m), 819.84(m), 796.14(m), 721.68(m) $cm^{-1}$ |
| HOTFAC | 2958.9(m), 2930.1(s), 2858.8(m), 1595.7(s), 1455.8(m), 1378.9(m), 1353.7(m), 1342.4(m), 1279.8(s), 1202.1(s), 1157.8(s), 1108.8(s), 886.63(m), 801.39(m) $cm^{-1}$ |
| GTFAC and NTFAC | 2960(m), 2905(m), 2850(m), 1590(s), 1450(m), 1275(s), 1195(s), 1150(s), 875(m), 795(m) $cm^{-1}$ |

TABLE 2-continued

| IR Spectra for TFAC Derivatives (KBr plates, neat films) | |
|---|---|
| Ligand | IR |
| (identical) FTFAC | 2950(s), 2910(s), 2850(s), 1590(s), 1450(s), 1375(m), 1275(s), 1200(s), 1155(s), 1110(s), 880(m), 830(m), 800(m) $cm^{-1}$ |

TABLE 3

| Elemental Analysis Data for TFAC Derivatives | |
|---|---|
| OTFAC | Calc'd for $C_{10}H_{13}F_3O_2$; C 54.05; H 5.90; F 25.65; O 14.40 Found: C 54.17; H 6.1; F 24.50 |
| ATFAC | Calc'd for $C_8H_9F_3O_2$: C 49.49; H 4.67; F 29.36; O 16.48 Found: C 50.04; H 4.82; F 23.3 |
| NTFAC | Calc'd for $C_{15}H_{21}F_3O_2$: C 62.05; H 7.29; F 19.63; O 11.02 Found: C 61.70; H 7.33 |
| HOTFAC | Calc'd for $C_{17}H_{23}F_3O_2$: C 63.73; H 8.49; F 17.79; O 9.99 Found: C 64.04; H 8.40; F 13.3 |
| FTFAC | Calc'd for $C_{20}H_{24}F_3O_2$: C 67.58; H 7.37 Found: C 65.45; H 8.10 |

EXAMPLE 2

Preparation of Solid $Cu^I$ Complexes of TFAC Ligands

One equivalent of free ligand is mixed with one half equivalent of cuprous oxide under a nitrogen atmosphere. The period for reaction varies from a few minutes (ATFAC) to a few hours (GTFAC), the end of the reaction being determined by solidification of the reaction mixture. HOTFAC does not produce a solid product after stirring overnight, but produces a solid product upon addition of carbon monoxide to the reaction mixture.

The resulting solid product is broken up and washed with hexane until no further blue material ($Cu^{II}$) is leached out. Toluene is added to the residue, using about 200 mL of toluene/g of solid, in a Schlenk flask equipped with a rubber septum. Ethylene gas is bubbled into the suspension for a few minutes under atmospheric pressure with stirring to solubilize the $Cu^I$ complex. During the process, the mixture becomes more transparent and it is thought that the suspended solid is mostly cuprous oxide.

The resulting solution is filtered through celite (Aldrich Chemical Co.) to produce a faintly yellow solution, evaporation of which gives pale yellow pure crystalline $Cu^I$ complex. If the product appears to contain $Cu^{II}$ complex by being colored with a blue tint, rinsing with hexane will remove this.

It appears that best yields of pure $Cu^I$ complexes are obtained when no more than one half equivalent of cuprous oxide is used and when the cuprous oxide is at least 99.9% pure. Use of higher amounts of cuprous oxides appears to encourage disproportionation to $Cu^{II}$.

IR spectra, elemental analyses and NMR data for $Cu^I$ complexes of various TFAC ligands are given in Tables 4–6.

TABLE 4

| IR Spectra for $Cu^I$ Complexes of TFAC Derivatives | |
|---|---|
| $Cu^I$ Complex | IR (KBr pellet) |
| $Cu^I$GTFAC | 2981.3(m), 2967.0(m), 2940.6(m), 2915.8(m), 2906.5(m), 2848.9(m), 1634.7(s), 1615.1(s), 1526.7(s), 1507.4(s), 1498.2(s), 1304.4(m), 1287.4(s), 1253.0(m), 1175.6(s), 1158.3(s), 1149.5(s), 1138.3(s), 848.89(m), 759.36(m) $cm^{-1}$ |
| $Cu^I$OTFAC | 2975(m), 2940(m), 2900(m), 1603(s), 1520(s), 1460(s), 1280(s), 1180(s), 1145(s), 1070(m), 790(m), 580(m) $cm^{-1}$ |
| $Cu^I$HOTFAC | 2910(s), 2850(m), 1609(s), 1590(sh), 1510(m), 1460(s), 1280(s), 1190(s), 1140(s), 1070(m), 800(m) $cm^{-1}$ |
| $Cu^I$ATFAC | 2980(m), 2959(m), 2912(m), 1604(s), 1511(s), 1457(s), 1272(s), 1181(s), 1135(s) $cm^{-1}$ |

TABLE 5

| Elemental Analyses for $Cu^I$ Complexes of TFAC Derivatives | |
|---|---|
| $Cu^I$ Complex | Analysis |
| $Cu^I$OTFAC | Calc'd for $C_{10}H_{12}F_3O_2Cu$: C 42.18; H 4.25; F 20.02; Cu 22.32. Found: C 42.28; H 4.23; F 18.89, Cu 22.09 |
| $Cu^I$ATFAC | Calc'd for $C_8H_8F_3O_2Cu$: C 37.43; H 3.14; F 22.20; Cu 24.76. Found: C 37.83; H 3.14; F 22.20; Cu 24.60 |
| $Cu^I$HOTFAC | Calc'd for $C_{17}H_{26}F_3O_2Cu$: C 53.32; H 6.84; F 14.88; Cu 16.59. Found: C 55.68; H 7.20; F 17.95 |
| $Cu^I$GTFAC | Calc'd for $C_{15}H_{20}F_3O_2Cu$: C 51.06; H 5.71; F 16.15; Cu 18.01. Found: C 50.99; H 5.72; F 16.20; Cu 20.82 |

TABLE 6

| $^1H$ NMR Spectra for $Cu^I$ Complexes | |
|---|---|
| $Cu^I$ Complex | $^1H$ NMR |
| $Cu^I$OTFAC | $d_8$toulene + ethylene (~1 atm, 25° C.): 1.55 ppm (d, 6H); 2.17 ppm (m, 4H); 4.2 ppm (s, 6H)(ethylene), 5.05 ppm (m, 1H) (s, 1H); 5.8 ppm (s, 1H) |
| $Cu^I$ATFAC | $d_8$toulene + ethylene (~1 atm, 25° C.): 2.09 ppm (m, 4H); 4.05 ppm (s, ~3H)(ethylene); 5.13 ppm (m, 1H); 5.75 ppm (s, 1H) |
| $Cu^I$GTFAC | $CDCl_3$: 1.64 (s, 6H); 1.68 ppm (s, 3H); 2.17 ppm (s, 4H); 2.28 ppm (t, 2H); 2.37 ppm (d, 2H); 4.95 ppm (m, 2H); 5.57 ppm (s, 1H) |

EXAMPLE 3

Volumetric Gas Uptake Measurements for $Cu^I$TFAC Complexes

Volumetric gas uptake measurements are carried out in a glass apparatus provided with carbon monoxide and propylene feeds, metered through mercury bubblers, operatively connected to a vacuum line and to mercury gas burets for measuring gas volume changes, connected to a pressure transducer (MKS 1000 torr) for measuring absolute pressure readings and to a thermostatted sample chamber. In normal operation, the apparatus permitted measuring volume changes of ±0.007 $cm^3$, with errors in pressure and bath temperature of ±0.1 torr and ±0.2° C., respectively. The apparatus, other than the sample chamber, was not thermostatted, and was exposed to ambient temperature variations of ±0.5° C. during the course of a run. The sample of complex is sealed in a glass vial, containing sand and having a magnet sealed therein. Volume changes from 1–50 $cm^3$ at pressures of 50–1000 torr and temperatures of 40° C. to −50° C. could be measured using the apparatus.

In a representative run, 50–200 mg of sample is sealed in a break seal vial under 75–600 torr of the selected uptake gas. Sand is charged to the vial to minimize dead volume. A glass-encased magnetic stirring bar is attached to the break vial. The resulting sample is placed in a sample chamber (uptake flask) and the contents of the flask are degassed. Dry distilled ethylbenzene is added to the sample chamber using a syringe. The uptake flask is attached to the volumetric apparatus and the system is evacuated. The sample vial is suspended above the ethylbenzene, using an external magnet, and the ethylbenzene is stirred rapidly. The flask is immersed in a constant temperature bath (−25° C. to 40° C.) and brought to temperature. Ethylbenzene vapor pressure is allowed to equilibrate throughout the system. Upon reaching equilibrium (1–2 h), the pressure is recorded. The system is pressurized with uptake gas until the total pressure equals ethylbenzene vapor pressure plus pressure of uptake gas in the break vial. The system is allowed to come to equilibrium for 1.5–2.5 h with pressure adjustments to maintain the correct total pressure.

The gas buret is isolated and mercury levels in the buret columns, total pressure, room temperature and bath temperature are recorded. The break vial is dropped and broken to initiate gas uptake. Mercury levels of the gas buret are adjusted at 5–10 min intervals to bring total pressure back to the initially-measured total pressure.

After each adjustment, reaction time, total pressure, mercury levels and room and bath temperatures are recorded. Adjustments are made until no change in either mercury levels or total pressure is observed for 20–30 min. The measured change in mercury levels permits calculation of volume change, which in turn is related to moles of uptake gas absorbed. The equilibrium constant is calculated from molar uptake, total moles of complex and pressure of uptake gas.

Results for absorption of CO by $Cu^{I}$OTFAC are given in Table 7. Results for reversible absorption of CO by $Cu^{I}$GTFAC are shown in Table 8. In Table 9 are shown results of experiments on reversible absorption of propylene by $Cu^{I}$GTFAC.

These experiments show that $Cu^{I}$TFAC derivatives of this invention function as absorbents for carbon monoxide and for olefins. The results in Tables 7–9 are also shown in FIG. 1.

Other binding parameters for the complexes of this invention are calculated. The equilibrium constant is shown in terms of $P_{1/2}$ (gas), which is the pressure (in torr) of the gas, required for reaction of half of the complex. As shown in Table 10, the heat of binding for both CO and propylene is very low, about 2–3 kcal/mol. This low heat of binding means that attainment of the maximum (equilibrium) capacity of the absorbent system is favored. The complexes of this invention have a significantly lower heat of binding than the Cosorb cuprous tetrachloroaluminate tolene complexes in commercial use, as further shown in Table 10.

Example 4

(a) Synthesis of 1,1,1-Trifluoro-3-trifluoroacetyl-5-hexene-2-one (Allylhexafluoroacetylacetone)

To a Schlenk tube equipped with a septum and stirring bar is charged silver oxide (6.13 g, 0.026 mol). The tube is degassed. Diethyl ether (60 mL) is added by a cannula and the mixture is stirred to produce a black suspension. Hexafluoroacetylacetone (7.2 mL, 0.051 mol) is slowly added from a syringe over 15 min, during which an exotherm is observed. The resulting mixture is stirred for 1.5 h and then filtered through diatomaceous earth on a medium porosity Schlenk frit to give a slightly yellow solution. Solids on the filter are washed with diethyl ether (three 20-mL portions). The combined filtrate and washings are evaporated under vacuum to leave an off-white solid.

TABLE 7

Reversible CO Absorption Data for $Cu^{I}$OTFAC in Ethylbenzene

| $[Cu]^T$(M) | $P_{CO}$(torr) | % Cu(CO) | $K_{eq}$(torr$^{-1}$) | T(K) | $-\ln K_{eq}$ | 1/T(K$^{-1}$) |
|---|---|---|---|---|---|---|
| $1.77 \times 10^{-2}$ | 191.1 | 46.2 | $4.5 \pm 0.1 \times 10^{-3}$ | 254.2 | 5.40 | $3.93 \times 10^{-3}$ |
| $1.94 \times 10^{-2}$ | 373.0 | 53.5 | $3.09 \pm 0.06 \times 10^{-3}$ | 275.8 | 5.78 | $3.62 \times 10^{-3}$ |
| $2.33 \times 10^{-2}$ | 276.9 | 40.5 | $2.46 \pm 0.06 \times 10^{-3}$ | 295.2 | 6.00 | $3.39 \times 10^{-3}$ |
| $1.12 \times 10^{-2}$ | 158.5 | 24.5 | $2.05 \pm 0.06 \times 10^{-3}$ | 310.2 | 6.19 | $3.22 \times 10^{-3}$ |

System: $Cu^{I}$OTFAC + CO 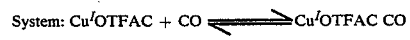 $Cu^{I}$OTFAC CO $$\text{where } K_{eq} = \frac{[Cu^{I}OTFAC \cdot CO]}{[Cu^{I}OTFAC][CO]}$$

TABLE 8

Reversible CO Absorption Data for $Cu^{I}$GTFAC in Ethylbenzene

| $[Cu]^T$(M) | $P_{CO}$(torr) | % Cu(CO) | $K_{eq}$(torr$^{-1}$) | T(K) | $-\ln K_{eq}$ | 1/T(K$^{-1}$) |
|---|---|---|---|---|---|---|
| $1.77 \times 10^{-2}$ | 183.7 | 75.6 | $1.68 \pm 0.07 \times 10^{-2}$ | 253.2 | 4.08 | $3.95 \times 10^{-3}$ |
| $1.97 \times 10^{-2}$ | 107.3 | 57.8 | $1.28 \pm 0.03 \times 10^{-2}$ | 276.2 | 4.36 | $3.62 \times 10^{-3}$ |
| $1.17 \times 10^{-2}$ | 80.8 | 44.4 | $0.99 \pm 0.03 \times 10^{-2}$ | 295.0 | 4.62 | $3.39 \times 10^{-3}$ |
| $1.30 \times 10^{-2}$ | 240.0 | 70.1 | $0.79 \pm 0.03 \times 10^{-2}$ | 309.2 | 4.84 | $3.23 \times 10^{-3}$ |

System: $Cu^{I}$GTFAC + CO 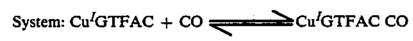 $Cu^{I}$GTFAC CO $$\text{where } K_{eq} = \frac{[Cu^{I}GTFAC \cdot CO]}{[Cu^{I}GTFAC][CO]}$$

TABLE 9

Reversible Propylene Absorption Data for $Cu^{I}$GTFAC in Ethylbenzene

| $[Cu]^T$(M) | $PC_3H_6$ (torr) | % Cu ($C_3H_6$) | $K_{eq}$(torr$^{-1}$) | T(K) | $-\ln K_{eq}$ | 1/T(K$^{-1}$) |
|---|---|---|---|---|---|---|
| $1.82 \times 10^{-2}$ | 106.3 | 77.4 | $3.2 \pm 0.3 \times 10^{-2}$ | 263.2 | 3.45 | $3.80 \times 10^{-3}$ |

TABLE 9-continued

Reversible Propylene Absorption Data for $Cu^I$GTFAC in Ethylbenzene

| $[Cu]^T$(M) | $PC_3H_6$ (torr) | % Cu ($C_3H_6$) | $K_{eq}$(torr$^{-1}$) | T(K) | $-\ln K_{eq}$ | 1/T($K^{-1}$) |
|---|---|---|---|---|---|---|
| $2.27 \times 10^{-2}$ | 99.9 | 73.0 | $2.7 \pm 0.1 \times 10^{-2}$ | 275.5 | 3.61 | $3.63 \times 10^{-3}$ |
| $1.43 \times 10^{-2}$ | 136.3 | 72.6 | $1.94 \pm 0.08 \times 10^{-2}$ | 294.0 | 3.94 | $3.40 \times 10^{-3}$ |
| $1.76 \times 10^{-2}$ | 213.3 | 75.4 | $1.44 \pm 0.05 \times 10^{-2}$ | 312.0 | 4.24 | $3.20 \times 10^{-3}$ |
| $4.89 \times 10^{-2}$ | 577.3 | 90.6 | $1.67 \pm 0.08 \times 10^{-2}$ | 291.5 | 4.09 | $3.43 \times 10^{-3}$ |

System: $Cu^I GTFAC + C_3H_6 \rightleftharpoons Cu^I GTFAC\ C_3H_6$ where $K_{eq} = \frac{[Cu^I GTFAC \cdot C_3H_6]}{[Cu^I GTFAC][C_3H_6]}$

TABLE 10

Gas Uptake Parameters in Ethylbenzene

| Complex | Gas | $P_{1/2}$ (torr) | ΔH (kcal/mol at 295° K.) |
|---|---|---|---|
| Cosorb | CO | 79 | −6 |
| $Cu^I$OTFAC | CO | 402 | $-2.2 \pm 0.2$ |
| $Cu^I$GTFAC | CO | 101 | $-2.1 \pm 0.2$ |
| $Cu^I$GTFAC | $C_3H_6$ | 52 | $-2.6 \pm 0.2$ |

The solid is redissolved in 60 mL of diethyl ether and the resulting solution is cooled to −78° C. in a dry ice-isopropanol bath. To an addition funnel is charged diethyl ether (20 mL) and allylbromide (4.4 mL, 0.051 mol). This solution is added dropwise to the cold solution of silver hexafluoroacetylacetate. After about half the allyl bromide is added, a precipitate is formed in the reaction vessel. After all the allyl bromide is added, the reaction mixture is allowed to warm to room temperature under a stream of nitrogen. The product is filtered under ambient conditions to remove precipitated silver bromide. The solids on the filter are washed with three 50-mL portions of diethyl ether. The combined filtrate and washings are evaporated on a rotating evaporator to a volume of about 125 mL. The remaining material is distilled under nitrogen. The highest boiling fraction (108° C./760 torr) is identified as allylhexafluoroacetylacetone. The yield is 6.38 g (0.026 mol, 51%).

Anal. Calc'd for $C_8H_6F_6O_2$: C 38.73; H 2.44. Found: C 38.75, 38.62; H 2.44, 2.47.

IR (neat film): C═O, 1779 (s) and 1753 (s) cm$^{-1}$; C═C, 1642 (w) cm$^{-1}$.

$^1$H NMR (in $CDCl_3$): 2.74 ppm(t, 2H); 4.51 ppm (t, 1H); 5.16 ppm (m, 2H); 5.68 ppm (m, 1H) δ TMS.

(b) Preparation of $Cu^I$ Allylhexafluoroacetylacetonate

Allyl hexafluoroacetylacetonate (AHFAC) is reacted with $Cu_2O$ as in Example 2 to a give a solid product. The $Cu^I$ complex is isolated as in Example 2, in the form of a pale yellow powder, which binds both ethylene and CO reversibly in toluene solution. However, $Cu^I$AFHAC is insoluble in toluene until CO or ethylene is added to the system.

We claim:

1. A compound of the formula

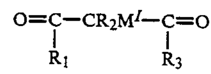

wherein $R_1$ is trichloromethyl or $R_F$; $R_F$ is $C_nF_{2n+1}$ and n is 1–8; $R_2$ is H or hydrocarbyl of 2–20 carbon atoms having from one to three olefinic unsaturated bonds; $R_3$ is hydrocarbyl of 2–20 carbon atoms having from one to three olefinic unsaturated bonds and $M^I$ is $Cu^I$ or $Ag^I$.

2. A compound of claim 1, wherein $M^I$ is $Cu^I$, $R_1$ is $R_F$ and $R_2$ is H.

3. A compound of claim 1, wherein $M^I$ is $Cu^I$, $R_1$ is $CF_3$ and $R_2$ is H.

4. A compound of claim 1, wherein $M^I$ is $Cu^I$, $R_1$ is $CF_3$ and $R_3$ is 2-butenyl, 2-methyl-2-pentenyl, (E)-2,6-dimethyl-2,6-nonadienyl or 5-(2-methyl-2-dodecenyl).

5. Copper (I) 1,1,1-trifluoro-8,12-dimethyl-trans-7,11-tridecadiene-2,4-dioneate, a compound of claim 1.

6. Copper(I) 1,1,1-trifluoro-8-methyl-7-nonene-2,4-dioneate, a compound of claim 1.

7. Copper(I) 1,1,1-trifluoro-5-prenyl-dodecane-2,4-dioneate, a compound of claim 1.

8. Copper(I) 1,1,1-trifluoro-7-octene-2,4-dioneate, a compound of claim 1.

9. A compound of the formula $$\begin{array}{c} O{=}C{-}CRM^I{-}C{=}O \\ |\qquad\qquad | \\ R_F \qquad\quad R_{F'} \end{array}$$

wherein $R_F$ and $R_{F'}$ are independently selected from perfluoroalkyl of 1–8 carbon atoms; R is hydrocarbyl of 2–20 carbon atoms having from one to three olefinic unsaturated bonds and $M^I$ is $Cu^I$ or $Ag^I$.

* * * * *